United States Patent [19]

Tarchini

[11] Patent Number: 4,671,798
[45] Date of Patent: Jun. 9, 1987

[54] 1,2,3,4,4A,5,8,8A-OCTAHYDRO-2,2,6,8-TETRAMETHYL-1-NAPHTHALENOL, ITS USE AS PERFUMING INGREDIENT AND PROCESS FOR MAKING SAME

[75] Inventor: Claudio Tarchini, Carouge, Switzerland

[73] Assignee: Firmenich SA, Geneva, Switzerland

[21] Appl. No.: 716,078

[22] Filed: Mar. 26, 1985

[30] Foreign Application Priority Data

Jul. 12, 1984 [CH] Switzerland ............... 3376/84

[51] Int. Cl.⁴ ............... D06P 3/80; C07C 35/22; C11D 17/00; C11D 9/00
[52] U.S. Cl. ............... 8/522; 568/374; 568/349; 568/817; 568/819; 252/89.1; 252/108
[58] Field of Search ............... 568/819, 817, 374, 349; 8/522 R

[56] References Cited

U.S. PATENT DOCUMENTS 4,431,843  2/1984  Yoshida ............... 268/819

*Primary Examiner*—Paul Lieberman
*Assistant Examiner*—John F. McNally
*Attorney, Agent, or Firm*—Pennie & Edmonds

[57] ABSTRACT

Bicyclic carbinol of formula

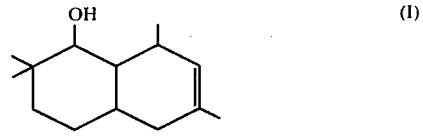

or 1,2,3,4,4a,5,8,8a-octahydro-2,2,6,8-tetramethyl-1-naphthalenol possesses useful odorous properties and it can be used advantageously as perfuming ingredient.

A two-step process for its synthesis is disclosed starting from 2-methylpenta-1,3-diene and 6,6-dimethylcyclohex-2-en-1-one.

5 Claims, No Drawings

1,2,3,4,4A,5,8,8A-OCTAHYDRO-2,2,6,8-TETRAMETHYL-1-NAPHTHALENOL, ITS USE AS PERFUMING INGREDIENT AND PROCESS FOR MAKING SAME

BRIEF SUMMARY OF THE INVENTION

The present invention provides a novel bicyclic carbinol of formula

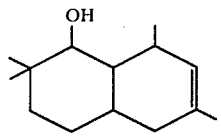

or 1,2,3,4,4a,5,8,8a-octahydro-2,2,6,8-tetramethyl-1-naphthalenol.

The invention provides further a perfume composition or a perfumed article which contains as fragrance active ingredient bicyclic carbinol of formula (I).

The invention relates also to a soap, a detergent or a fabric softener containing as fragrance active material an odor effective amount of the bicyclic carbinol of formula (I).

Further, the instant invention provides a process for the preparation of said bicyclic carbinol (I), which process comprises:

a. adding 2-methyl-penta-1,3-diene to 6,6-dimethyl-cyclohex-2-en-1-one under the conditions of a Diels-Alder type reaction to give 3,4,4a,5,8,8a-hexahydro-2,2,6,8-tetramethyl-1(2H)-naphthalenone, and b. reducing the obtained naphthalenone to give 1,2,3,4,4a,5,8,8a-octahydro-2,2,6,8-tetramethyl-1-naphthalenol by means of a carbonyl group reducing agent.

BACKGROUND OF THE INVENTION

Prior art discloses a class of hydroxy- and oxabicyclic compounds depicted by the following generic formula

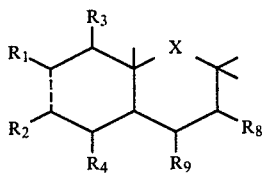

wherein the dotted line stands for a carbon-carbon single or double bond and wherein:

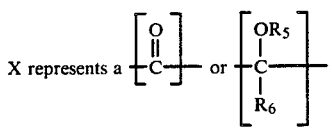

and $R_1$, $R_2$, $R_3$, $R_4$, $R_8$ and $R_9$ represent a hydrogen or a methyl group provided that (i) three at least of groups $R_1$, $R_2$, $R_3$ and $R_4$ represents a hydrogen atom and (ii) when the dotted line designates a carbon-carbon single bond and X is

one of substituents $R_1$ to $R_4$ is a methyl and the others are hydrogen;

$R_5$ represents a hydrogen, MgZ or Li;

Z represents chloro, bromo or iodo; and $R_6$ represents a hydrogen or a methyl radical [see European Pat. Appln published on Mar. 10, 1982 under Ser. No. 0047154].

Though it does not fall under the definition given in the cited document, the application mentions 1,2,3,4,4a,5,8,8a-octahydro-2,2,6,8(5,7),8a-pentamethyl-1-naphthalenol, a compound which, according to the applicants, occurs as a mixture of the following compounds

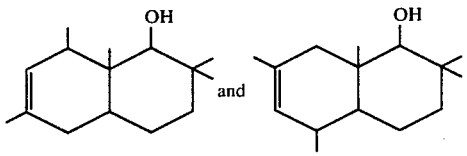

From the molecular point of view, their structure is analogous to that of compound (I) of the instant invention. However, in spite of this analogy, the prior known mixture and the product of the invention possess dissimilar odor properties. In fact, the described mixture develops a strong woody odor of patchouli type, accompanied by an ambery and musky scent, whereas compound (I) possesses a lifting and very powerful fruity odor character reminiscent of eucalyptus fruits or blackcurrant buds. It possesses moreover a citrus note reminiscent more particularly of grapefruit or lemon. Owing to certain of its characters, namely its slightly sulfury note, compound (I) is also reminiscent of exotic fruits, particularly of passion fruit. These fragrance characters are very surprising when compared with the cited prior known derivatives of analogous structure which, as mentioned above, typically develop a woody, patchouli type scent.

THE INVENTION

Owing to its properties, compound (I) can find a wide range of application. For instance, it can be utilized to enrich various perfume compositions of different nature, of citrus, chypre or fruity type.

It is perfectly suited to be used as a constituent in both alcoholic fragrances and functional products wherein, due to its stability, it finds a broad range of applications. Compound (I) therefore can be utilized to the perfuming of soap, cationic, anionic, zwitterionic or non-ionic detergents, fabric softeners, household materials, waxes, polishes in addition to cosmetics and shampoos. Of course, the compound of the invention can be used as sole fragrance ingredient, but typically it is used in admixture with current perfume coingredients. The nature of those coingredients is well known to the expert and a further discussion with respect thereto is deemed superfluous. Typically, one can use natural and synthetic ingredients as described in European Pat. Appln published under Ser. No. 0096243, disclosure of which is made therein by reference.

The concentrations at which compound (I) can achieve the desired effects can vary widely. The expert perfumer knows by experience that concentration values depend not only on the effect desired, but also on the nature of the coingredients present in a given composition and on that of the material it is desired to perfume.

Thus, concentrations of the order of 0.1–0.5% by weight, based on the total weight of the perfumed end-product, can achieve marked effects in the perfuming of soaps or detergents. When used in concentrated perfume bases, also known under the name of "perfume coeur", these values can be much higher, for instance of the order of about 2–5%, or even up to 10% or more of the weight of the composition into which they are added. As indicated above, compound (I) is a novel chemical entity. It can be prepared in accordance with a process analogous to that described in European Pat. Appln published under Ser. No. 0047154, starting from 6,6-dimethyl-cyclohex-2-en-1-one and 2-methyl-penta-1,3-diene according to the following reaction scheme:

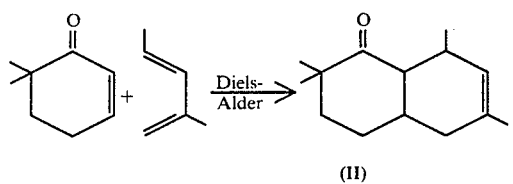

(II)

The bicyclic ketone thus obtained is then reduced by means of, for example, an alkali metal alumino-hydride such as lithium alumino-hydride. Other reducing agents, currently used to effect the reduction of carbonyl groups to hydroxyl, can also be used. Thus, it is possible to use sodium borohydride, sodium bis(2-methoxyethoxy)-aluminohydride (VITRIDE®, Eastman Kodak), or sodium diethylaluminohydride (OMH-1, Ethyl Corporation).

Diels-Alder type reactions are well known to proceed more efficiently in the presence of specific catalysts. Suitable catalysts include $AlCl_3$, $TiCl_4$, $FeCl_3$ or $HClO_4$. A Lewis acid such as $BF_3$, preferably in ethereal solution, is the catalyst of choice.

The reaction is effected at atmospheric pressure or at a pressure higher than the atmospheric pressure. In this latter case, the use of a catalyst is not necessary, especially when operating at temperatures above the room temperature, for example of the order of about 120°–200° C. The compound of the invention, prepared according to the process described above, can occur in cyclanic form cis (predominant) or trans.

Formula (I) is intended to define indifferently one or the other of the following isomers:

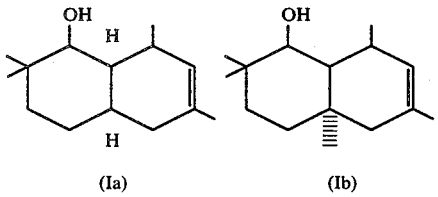

(Ia)        (Ib)

The spectroscopic analysis has not enabled us to detect the presence in the reaction mixture of the other possible positional isomer of formula

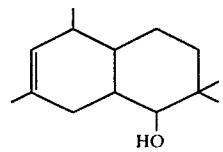

though its presence in minute amounts cannot be excluded.

On closer examination, it has become apparent that the main component of the obtained isomeric mixture is constituted, at about 75%, by isomer of formula

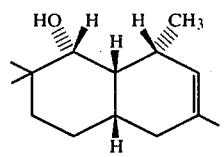

or 1,2,3,4,4aβ,5,8,8aβ-octahydro-2,2,6,8α-tetramethyl-1α-naphthalenol, which compound was accompanied by its stereoisomers for which the following structures are suggested:

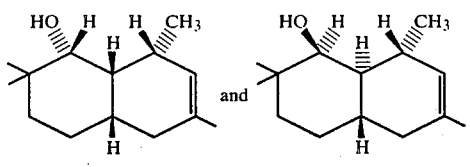

The invention is illustrated in a more detailed manner by the following examples wherein the temperatures are indicated in degrees centigrade and the abbreviations have the meaning common in the art.

EXAMPLE 1

Preparation of 1,2,3,4,4a,5,8,8a-octahydro-2,2,6,8-tetramethyl-1-naphthalenol a. 3,4,4a,5,8,8a-Hexahydro-2,2,6,8-tetramethyl-1(2H)-naphthalenone 124 G (1M) of 6,6-dimethyl-cyclohex-2-en-1-one, 200 ml of toluene and 10 ml of trifluoro-boro-etherate are placed under nitrogen atmosphere in a three-necked reaction vessel of 1000 ml capacity equipped with a thermometer and a stirrer. The mixture was cooled to 10° and 2-methyl-penta-1,3-diene was added thereto in small portions over 4 hours. After the addition was over, the mixture was left under stirring for 1 additional hour, whereupon it was hydrolyzed with an aqueous sodium carbonate solution. The excess of toluene was removed by means of a rotary evaporator under reduced pressure and the residue was distilled to give 101.7 g of the desired product having b.p. 70°–80°/26.6 Pa. A spectroscopic analysis indicated that the product obtained consisted of about 90% of isomer cis (a) and about 10% of trans (b).

NMR (360 MHz; $CDCl_3$): 0.99 (3H, s); 1.17 (3H, d, J=7); 1.23 (3H, s); 1.51 (1H, d of q, J=14 and 25); 1.61 (3H, broad s); 2.31 (1H, m); 2.47 (1H, m); 3.03 (1H, t, J=5); 5.23 (1H, broad s) δ ppm.

isomer (a)

MS:m/e: 206 (38), 191 (17), 173 (13), 159 (16), 135 (48), 107 (100), 91 (44).

isomer (b)

MS:m/e: 206 (39), 191 (18), 173 (16), 159 (22), 135 (66), 107 (100), 91 (42).

b. 1,2,3,4,4a,5,8,8a-octahydro-2,2,6,8-tetramethyl-1-naphthalenol

5 G (132 mM) of lithium-alumino-hydride and 80 ml of anhydrous diethyl ether were placed under nitrogen in a 1 l three-necked reaction vessel equipped with a mechanical stirrer, a reflux condenser and a thermometer. 86.6 G (420 mM) of the naphthalenone, obtained as described under letter a. above, in 150 ml of anhydrous ether were added during 1 h ½ to the suspension obtained cooled by an external ice bath. After termination of the addition, the reaction mixture was kept under stirring for 15 additional minutes, then it was slowly hydrolyzed by adding thereto 10% sulfuric acid until formation of two clear separated phases. After decantation and separation, the organic phase was washed until neutrality and concentrated under reduced pressure to give 84.1 g of a raw product which upon distillation yielded 80 g of the desired naphthalenol having b.p. 90°-100°/26.6 Pa.

NMR (360 MHz, CDCl$_3$): 0.91 (3H, s); 0.96 (3H, s); 1.11 (3H, d, J=7); 1.66 (3H, large s); 2.02 (1H, m); 2.26 (1H, m); 2.50 (1H, m); 4.77 (1H, large s); 5.59 (1H, large s) δ ppm.

isomer (a)

MS:m/e: 208 (3), 190 (37), 175 (48), 120 (70), 105 (100), 91 (28).

isomer (b)

MS:m/e: 208 (1), 190 (37), 175 (37), 120 (100), 105 (93), 91 (28).

6,6-Dimethyl-cyclohex-2-en-1-one, used as starting material in the above described process, can be prepared starting from isopropyl-methyl ketone and acrolein according to a condensation reaction in the presence of an acidic dehydrating agent as indicated hereinbelow:

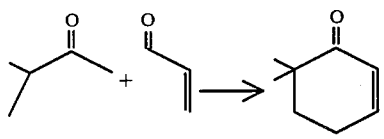

EXAMPLE 2

Perfuming of a soap base

100 G of soap base chips, obtained from a non-perfumed soap paste derived from coconut and tallow oil, were admixed with 1 g of the product obtained in Example 1. After homogeneisation, the soap paste was used to manufacture soap bars which were then subjected to the evaluation of a group of experts who expressed their opinion by saying that the fragrance of the thus perfumed soap was pleasantly fresh and fruity.

EXAMPLE 3

Cologne

A base perfume composition of Cologne type for men was obtained by mixing the following ingredients (parts by weight):

| | |
|---|---|
| Clary sage oil | 20 |
| Lavender oil | 150 |
| Synthetic bergamot | 200 |
| Lemon oil | 140 |
| Sweet orange oil | 40 |
| Synth. galbanum oil 10%* | 20 |
| Muscone 10%* | 50 |
| Methyl 2-pentyl-3-oxo-cyclopentylacetate | 10 |
| 1,1-Dimethyl-6-tert-butyl-4-acetylindane | 10 |
| α-Isomethylionone | 50 |
| Synth. Ylang | 80 |
| Synth. Jasmin | 25 |
| Synth. Geranium | 50 |
| Synth. Neroli | 100 |
| Coriander oil | 5 |
| Diethyl phthalate | 50 |
| | 1000 |

*in diethyl phthalate

By adding to the above base the compound obtained according to Example 1 at a concentration of 0.2% by weight, a novel composition resulted with a marked exalting effect.

EXAMPLE 4

Perfume composition for shampoos

A base perfume composition was prepared by mixing the following ingredients (parts by weight):

| | |
|---|---|
| Deterpeneted lemon oil (TETRAROME ®)[1] | 300 |
| 3,5,5-Trimethylhexyacetate | 200 |
| Litsea Cubeba oil | 200 |
| Limonene | 50 |
| Citronellol | 40 |
| Citronelle Java oil | 30 |
| α-Damascone 10%* | 30 |
| Geranontrile | 20 |
| HEDIONE ®[1] | 20 |
| Decanal 10%* | 20 |
| Undecanal 10%* | 20 |
| Dodecanal 10%* | 20 |
| Nonanal 10%* | 10 |
| Citronellyl formate | 10 |
| RHUBOFLOR ®[1] [2] | 5 |
| Nerolidol | 5 |
| Total | 980 |

*in diethyl phthalate
[1]origin: Firmenich SA, Geneva (Switzerland)
[2]see European Patent Appln n° 66684; 3-oxa-9-and 3-oxa-10-ethylidene-tricyclo[6.2.1.0$^{2,7}$]undecane.

By adding to the above base 20 g of the product obtained as described in Example 1, a novel composition resulted with an improved naturalness and an increased citrus fragrance note.

EXAMPLE 5

Perfume composition

A perfume composition was prepared by mixing the following ingredients (parts by weight):

| | |
|---|---|
| Benzyl salicylate | 150 |
| Musk ketone | 120 |
| Isomethyl-ionone[1](IRALIA ®) | 100 |
| Hydroxycitronella[1](CYCLOSIA BASE) | 100 |
| Phenethylol | 80 |
| Linalyl acetate | 60 |
| Synth. jasmin oil | 60 |
| Ylang coeur | 30 |
| Bergamot oil** | 30 |
| Clove oil | 30 |
| Oriental sandalwood oil | 30 |

| | -continued | |
|---|---|---|
| Synth. civet oil 1%* | | 30 |
| Synth. Rose of May oil | | 30 |
| Mimosa absolute | | 20 |
| Vetyveryl acetate | | 15 |
| Undecylenic aldehyde 10%* | | 15 |
| Isoeugenol | | 15 |
| α-Terpineol | | 15 |
| Cyclopentadecanolide[1] | | 10 |
| Styrallyl acetate | | 5 |
| Synth. Musk[1] | | 5 |
| Synth. Amber | | 5 |
| Cinnamic alcohol | | 5 |
| Total | | 960 |

*in dipropylene-glycol
[1]orgin: Firmenich SA, Geneva(Switzerland)
[2]**without furocoumarins By adding to the above base composition 40 g of a 10% solution of the product obtained as described in Example 1 in dipropylene-glycol, a novel composition resulted possessing a very fresh, lifting top note with an increased citrus character.

EXAMPLE 6

The product obtained as described in Example 1 was used to perfume the following articles at the concentration indicated.

| | Article | Concentration %[1] | Odor/appearance[2] |
|---|---|---|---|
| 1. | Cologne | 5 | S/N |
| 2. | Beauty cream | 0.4 | S/N |
| 3. | Shampoo | 0.5 | S/N |
| 4. | Deo-aerosol | 1.2 | S/N |
| 5. | Hair lacquer | 0.3 | S/N |
| 6. | Soap | 0.5 | S/N |
| 7. | Talc powder | 0.5 | S/N |
| 8. | Detergent powder | 0.2 | S/N |
| 9. | Chlorinated dish-washing detergent | 0.2 | S/N |

[1]parts by weight
[2]it reverts to the odor and appearance of the perfumed product after storage at 40° during 1 month.
S = Stable; N = normal color

What I claim is:
1. 1,2,3,4,4a,5,8,8a-Octahydro-2,2,6,8-tetramethyl-1-naphthalenol.

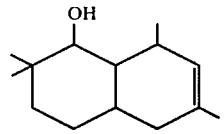

2. A perfume composition or a perfumed article containing as fragrance active ingredient the compound of claim 1.
3. As perfumed article according to claim 2, a soap, a detergent or a fabric softener.
4. A process for the preparation of the compound of claim 1, which comprises:
 a. adding 2-methyl-penta-1,3-diene to 6,6-diemthyl-cyclohex-2-en-1-one under the conditions of a Diels-Alder type reaction to give 3,4,4a,5,8,8a-hexahydro-2,2,6,8-tetramethyl-1(2H)-naphthalenone, and
 b. reducing the obtained naphthalenone to give 1,2,3,4,4a,5,8,8a-octahydro-2,2,6,8-tetramethyl-1-naphthalenol by means of carbonyl group reducing agent.
5. A process according to claim 4 wherein the reducing agent is lithium aluminohydride.

* * * * *